United States Patent [19]
Reading

[11] Patent Number: 5,248,199
[45] Date of Patent: Sep. 28, 1993

[54] METHOD AND APPARATUS FOR SPATIALLY RESOLVED MODULATED DIFFERENTIAL ANALYSIS

[75] Inventor: Michael Reading, London, England

[73] Assignee: TA Instruments, Inc., New Castle, Del.

[21] Appl. No.: 888,933

[22] Filed: May 26, 1992

Related U.S. Application Data

[63] Continuation-in-part of Ser. No. 844,448, Mar. 2, 1992.

[51] Int. Cl.5 ............................................. G01N 25/00
[52] U.S. Cl. ......................................... 374/11; 374/31
[58] Field of Search ...................... 374/10, 11, 12, 13, 374/31, 33, 36, 43, 110, 124, 166; 358/110

[56] References Cited

U.S. PATENT DOCUMENTS

| | | | |
|---|---|---|---|
| 2,975,629 | 3/1961 | Herbert | 374/166 |
| 3,263,484 | 8/1966 | Watson et al. | 374/11 |
| 3,271,996 | 9/1966 | Paulik et al. | 374/11 |
| 3,339,398 | 9/1967 | Barrall et al. | 374/11 |
| 3,360,993 | 1/1968 | MacMillan | 374/10 |
| 3,789,662 | 2/1974 | Zettler et al. | 374/31 |
| 4,255,961 | 3/1981 | Biltonen et al. | 374/11 |
| 4,690,569 | 9/1987 | Veitch | 374/12 |
| 4,747,698 | 5/1988 | Wickramasinghe et al. | 374/124 |
| 4,783,174 | 11/1988 | Gmelin et al. | 374/11 |
| 4,838,706 | 6/1989 | Coey et al. | 374/33 |
| 4,840,496 | 6/1989 | Elleman et al. | 374/124 |
| 5,046,858 | 9/1991 | Tucker | 374/166 |

OTHER PUBLICATIONS

O. L. Mayorga, W. W. van Osdol, J. L. Lacomba and E. Freire, "Frequency Spectrum of Enthalpy Fluctuations Associated With Macromolecular Transitions," Proc. Natl. Acad. Sci. USA, vol. 85, Dec. 1988, pp. 9514–9518.

P. Sullivan and G. Seidel, "Steady State, ac-Temperature Calorimetry," Physical Review, vol. 173, No. 3, Sep. 15, 1968, pp. 679–685.

N. Birge, and S. Nagel, "Specific-Heat Spectroscopy of the Glass Transition," Physical Review Letters, vol. 54, No. 25, Jun. 24, 1985, pp. 2674–2677.

N. Birge, "Specific-heat Spectroscopy of Glycerol and Propylene Glycol Near the Glass Transition," Physical Review B, vol. 34, No. 3, Aug. 1, 1986, pp. 1631–1642.

Jung, D. H., Kwon, T. W.; Bae, D. J.; Moon, I. K., and Jeong, Y. H., "Fully Automated Dynamic Calorimeter" Meas. Sci. Technol., vol. 3, 1992, pp. 475–484.

N. Birge and S. Nagel, "Wide Frequency Specific Heat Spectrometer," Rev. Sci. Instrum., vol. 58, Aug. 1987, pp. 1464–1470.

R. Garcia, "Scanning Tunneling Microscopy in Biology: Changing the Pace," Microscopy and Analysis, Jul. 1991, pp. 27–29.

I. Hatta and A. Ikushima, "Studies on Phase Transitions by AC Calorimetry," Japanese Journal of Applied Physics, Nov. 1981, pp. 1995–2011.

(List continued on next page.)

Primary Examiner—William A. Cuchlinski, Jr.
Assistant Examiner—G. Bradley Bennett
Attorney, Agent, or Firm—Kirkland & Ellis

[57] ABSTRACT

The present invention is a spatially-resolved differential analysis technique. A modulated differential analysis technique is applied using a proximal probe to obtain a spatially resolved characterization of a heterogeneous sample comprising at least two phases. As applied to spatially-resolved modulated differential scanning calorimetry, the present invention comprises a thermocouple probe that is scanned over the sample surface. The differential temperature of the area of the sample just beneath the thermocouple probe is obtained with respect to the temperature of a reference. The temperature of the sample and the reference is modulated above and below a transition temperature for one phase of the sample. The signal from the thermocouple probe is deconvoluted to obtain an image of the sample delineating the regions of the sample having that phase.

72 Claims, 3 Drawing Sheets

OTHER PUBLICATIONS

M. Hietschold, P. K. Hansma and A. L. Weisenhorn, "Scanning-Probe-Microscopy and Spectroscopy in Materials Science," Microscopy and Analysis, Sep. 1991, pp. 25–27.

S. MacPherson, "Atomic Resolution," Laboratory News, Mar. 19, 1990.

M. J. Miles, "The Application of STM/AFM to Biological Molecules," Microscopy and Analysis, Jul. 1990, pp. 7–9.

A. Rosencwaig, "Photoacoustic Microscopy," International Laboratory, Sep./Oct. 1979, pp. 37–43.

N. F. van Hulst, F. B. Segerink, "Optical Microscopy Beyond the Diffraction Limit," Microscopy and Analysis, Jan. 1992, pp. 21–23.

C. C. Williams and H. K. Wickramasinghe, "Photothermal Imaging with Sub-100-nm Spatial Resolution," Photoacoustic and Photothermal Phenomena Proceedings, pp. 364–368.

H. Yao and I. Hatta, "An AC Microcalorimeter Method for Precise Heat Capacity Measurement in a Small Amount of Liquid," Japanese Journal of Applied Physics, Jan. 1988, pp. 121–122.

Ulvac Sinku-Riko, Inc. Product Brochure ACC-1, "AC Calorimeter," publication date unknown, Catalog No. 8909-A13E/90.71000.

Ulvac Sinku-Riko, Inc. Product Brochure, "Thermal Constants Analyzer by AC Calorimetric Method," publication date unknown, Catalog No. 9010-PITR1/90.10.3000.

Ulvac Sinku-Riko, Inc. Product Brochure ACC-VL1, "AC Calorimeter," publication date unknown, Catalog No. 9102-A24E.

Microscopy and Analysis, "Aris Scanning Tunneling Microscope," Jan. 1992.

Di Product Brochure, "Nanoscope II, Scanning Tunneling Microscope," publication date unknown.

Struers Product Brochure, "Welcome to the World of Atoms, Tunnelscope 2400," publication date unknown.

Struers Product Brochure, "Welcome to the World of Atoms, Tunnelscope 2400, Software Version 2.0," publication date unknown.

METHOD AND APPARATUS FOR SPATIALLY RESOLVED MODULATED DIFFERENTIAL ANALYSIS

The present application is a continuation-in-part of application Ser. No. 07/844,448, filed on Mar. 2, 1992 ("the parent application"), which is expressly incorporated by reference herein. The present application combines the modulation techniques disclosed in the parent application with proximal probe techniques to produce spatially resolved characterized images of the sample.

BACKGROUND

1. Field of the Invention

The present invention relates to spatially resolved differential analytical techniques for determining the composition, phase, structure, or other properties of a sample of material.

2. Background of the Invention

Thermal analysis techniques generally comprise measuring a physical parameter as a function of the temperature of the sample. The sample temperature is strictly controlled throughout the analysis. Whenever the sample undergoes a chemical transformation, a physical transformation, a phase change, or another transition which affects the physical parameter being measured, the changes in that physical parameter may be interpreted to analyze the composition, structure, or thermal stability of the sample.

In differential thermal analysis techniques, the physical parameter of the sample being measured is compared to that of a reference, as a function of the temperature of the sample. The difference in the physical parameter measured for the sample and that measured for the reference is then recorded. The differential thermal analysis technique compensates for the effects of heating rate and ambient conditions that could cause changes in the measured physical parameter of the sample and reference. The differential thermal analysis technique can increase the sensitivity of the measurement of the physical parameter by removing large offsets in the value of the physical parameter whenever the precision of the measuring apparatus is limited.

Proximal-probe techniques such as Scanning Tunneling Microscopy and Atomic Force Microscopy obtain spatially-resolved characterization data by bringing a very small probe very close to the sample surface. These techniques are described, for example, in M. Hietschold, P. K. Hansma and A. L. Wiesenhorn, "Scanning-Probe-Microscopy and Spectroscopy in Materials Science," *Microscopy and Analysis*, September, 1991, pp. 25-27; and N. F. van Hulst and F. B. Segerink, "Optical Microscopy Beyond the Diffraction Limit," *Microscopy and Analysis*, January, 1992, pp. 21-23. Companies producing Scanning Tunneling Microscopes include Digital Instruments, Santa Barbara, Calif.; Burleigh Instruments, Fishers, N.Y.; and Struers, Westlake, Ohio.

C. C. Williams and H. K. Wickramasinghe, "Photothermal Imaging with Sub-100-nm Spatial Resolution," published in *Photoacoustic and Photothermal Phenomena, Proceedings*, P. Hess and J. Pelzl, eds., Springer Ser. Opt. Sci. v. 58, pp. 364-369 (1988) is incorporated by reference herein. This article describes a high resolution thermal microscope using a thermocouple probe.

High resolution analytical techniques are described in U.S. patent application Ser. No. 07/638,847, which is incorporated by reference herein. Those techniques seek to improve the resolution of changes in a characterizing physical parameter by controlling the rate of sample heating during transitions as a function of the rate of change of the physical parameter. When non-differential thermal analysis techniques are used, the high resolution techniques are effective in improving resolution for many transitions. However, they usually reduce the sensitivity of transitions when applied to differential thermal analysis techniques. This is because, for most differential thermal analysis techniques, the magnitude of the differential physical parameter is a direct function of the heating rate. Reducing the heating rate during transitions causes the differential signal to change, which may alter or obscure the true differential signal resulting from the transition event. This obscuring of the physical parameter can reduce the utility of the high resolution techniques when applied to conventional differential thermal analysis techniques.

Conventional differential thermal analysis techniques are limited in their ability to separate non-reversible events caused by enthalpic processes (chemical or physical) from reversible events such as changes in the heat capacity of the sample. This is because the reversible and non-reversible processes often occur simultaneously, or occur severely overlapped in time and/or temperature.

In addition, conventional and high resolution thermal analysis techniques cannot distinguish between rapidly reversible and non-rapidly reversible transitions within a single heating or cooling scan of the sample.

DEFINITIONS

"Transition" or "Transformation", as used herein, mean any type of physical or chemical transformation, phase change, or structural change in a material.

"Analyzing", as used herein with respect to materials, means determining the composition, phase, structure, and/or identification of the material.

"Characterizing differential physical parameter", as used herein, means the dependent differential physical parameter characterizing the sample, such as its heat flow, weight change, or change in dielectric or mechanical properties.

"Characterized image", as used herein with respect to a sample, means an image of a sample wherein the contrast in the image is caused by changes in the characterizing physical parameter as a function of position on the sample.

"Modulation temperature", as used herein, means the average value of the temperature of the sample during one modulation cycle.

"Modulation value", as used herein, means the average value of the driving variable during one modulation cycle.

"Driving variable", as used herein, means the independent physical parameter, such as temperature, pressure, applied stress, or wavelength of incident radiation, that is being used to drive a material through a transition. For example, in thermal analysis techniques such as DSC, temperature is typically the driving variable.

"Rapidly reversible", as used herein, means any portion of a signal, transition, or event which is a direct function of the rate of change of the driving variable. For example, the contribution to the heat flow signal in DSC attributable to the rate of change of temperature of the sample material is a rapidly reversible transition. In DSC, for example, one of the contributions to the rapidly reversible portion of the heat flow signal is the heat capacity of the sample material. Rapidly reversible processes include those processes which are thermodynamically reversible and can occur rapidly relative to the rate of change of the driving variable.

"Non-rapidly reversible", as used herein, means any portion of a signal, transition or event which is a direct function of the value of the driving variable. For example, the contribution to the heat flow signal in DSC attributable to the absolute temperature of the sample material is a non-rapidly reversible transition. This might be caused by a chemical or physical change taking place such as recrystallization. Non-rapidly reversible processes include those processes which are thermodynamically irreversible, as well as processes which are thermodynamically reversible, but which reverse very slowly relative to the rate of change of the driving variable due to the kinetic limitations of the process.

"Deconvolution", as used herein, means the process of separating the dependence of a characterizing physical parameter on a driving variable into two or more component parts so that the component parts can be utilized or analyzed separately, or compared with each other. For example, the dependence of a characterizing physical parameter can be deconvoluted into rapidly reversible and non-rapidly reversible components.

"Signal baseline", as used herein, means that portion of a signal representing the value of a characterizing physical parameter obtained in a range in which there are no transitions or transformations.

"Sensitivity" of an analytical technique, as used herein, means the degree to which signals associated with transitions can be physically distinguished from the signal baseline in the analytical data produced by the technique. This quality of the analytical technique is most critical when the value of the driving variable is changing very slowly.

"Resolution" of an analytical technique, as used herein, means the degree to which signals associated with different transitions can be physically separated in the analytical data produced by the technique. This quality of the analytical technique is most critical when multiple transitions occur at closely spaced values of the driving variable.

SUMMARY OF THE INVENTION

The present invention is a spatially-resolved modulated differential analytical instrument and technique. This instrument can measure sample characteristics as a function of position on a sample, rather than only as a function of time or only as a function of the driving variable. The instrument comprises a differential analytical apparatus as disclosed in the parent application, wherein the characterizing physical parameter is determined as a function of the position of a probe on or near the surface of a sample, thus providing a characterized image of the sample.

The present invention will be described herein using differential scanning calorimetry as the prototypical differential analytical technique. However, the present invention may be used with any appropriate differential analytical technique, including Pressure Differential Scanning Calorimetry (PDSC), Differential Thermal Analysis (DTA), Pressure Differential Thermal Analysis (PDTA), Differential Photocalorimetry (DPC), and Pressure Differential Photocalorimetry (PDPC).

The present invention, as applied to spatially-resolved modulated differential scanning calorimetry, comprises a modulated differential scanning calorimeter, as described in the parent application, wherein a thermocouple probe is scanned over the surface of the sample in close proximity to the sample, as the temperature of the sample is modulated. As the thermocouple probe is scanned, it detects differences in the temperature of the sample corresponding to the thermal properties of the material. The present invention could be practiced with other differential analytical techniques, using temperature sensing, capacitance, magnetic, piezoelectric, optical or acoustic probes, as discussed below.

In one embodiment of the invention, the temperature of the sample is modulated as the thermocouple probe is scanned over the surface of the sample. If the sample includes crystalline regions and amorphous regions, maximal contrast could be obtained by modulating the temperature of the sample above and below a transition temperature such as the melting point of the crystalline material. A plot of the thermocouple probe's response as a function of sample position would then provide an image delineating the crystalline regions from the amorphous regions. The contrast in the image would derive from the different responses of the crystalline and amorphous phases, respectively, to the oscillating temperature.

In a second embodiment, the sample temperature is varied at two frequencies, a modulation frequency and an oscillation frequency. The oscillation frequency would be selected to be different from the modulation frequency by at least a factor of 3, and preferably by at least a factor of 5. For example, if the modulation frequency is $f_m$, the oscillation frequency should be $0.2f_m$ or lower, or $5f_m$ or higher. As a general rule, the oscillation frequency would be lower than the modulation frequency. If the sample contained regions of a polymer phase having a glass transition temperature $T_g$, the polymer regions would be delineated by oscillating the temperature of the sample above and below $T_g$. The region of the sample changing its response in phase with the oscillation frequency would be identified as the polymer phase having that specific $T_g$.

In a third embodiment of the present invention, the probe is held in one position, above a previously delineated domain. The domain may be representative of many other domains exhibiting similar contrast in the characterized image. The temperature of the sample is then scanned to measure the transition temperature of that domain. The value of the transition temperature could then be used to identify the composition of that domain, and of all similar domains.

The reference thermocouple in differential scanning calorimetry is generally placed in thermal contact with a separate reference material. However, in spatially-resolved differential scanning calorimetry, the reference thermocouple may be placed in contact with the sample itself, either on the same surface as the scanning thermocouple, or on another surface of the sample.

A first object of the present invention is to provide an apparatus and a method for obtaining spatially-resolved characterized images of samples.

A second object of the present invention is to provide a differential thermal analysis technique which can be used to identify different regions in a sample.

A third object of the present invention is to provide an imaging method that does not require extensive sample preparation.

These and other objects of the present invention are described in greater detail in the detailed description of the invention, the appended drawings and the attached claims.

DETAILED DESCRIPTION OF THE INVENTION

Figure 1A:
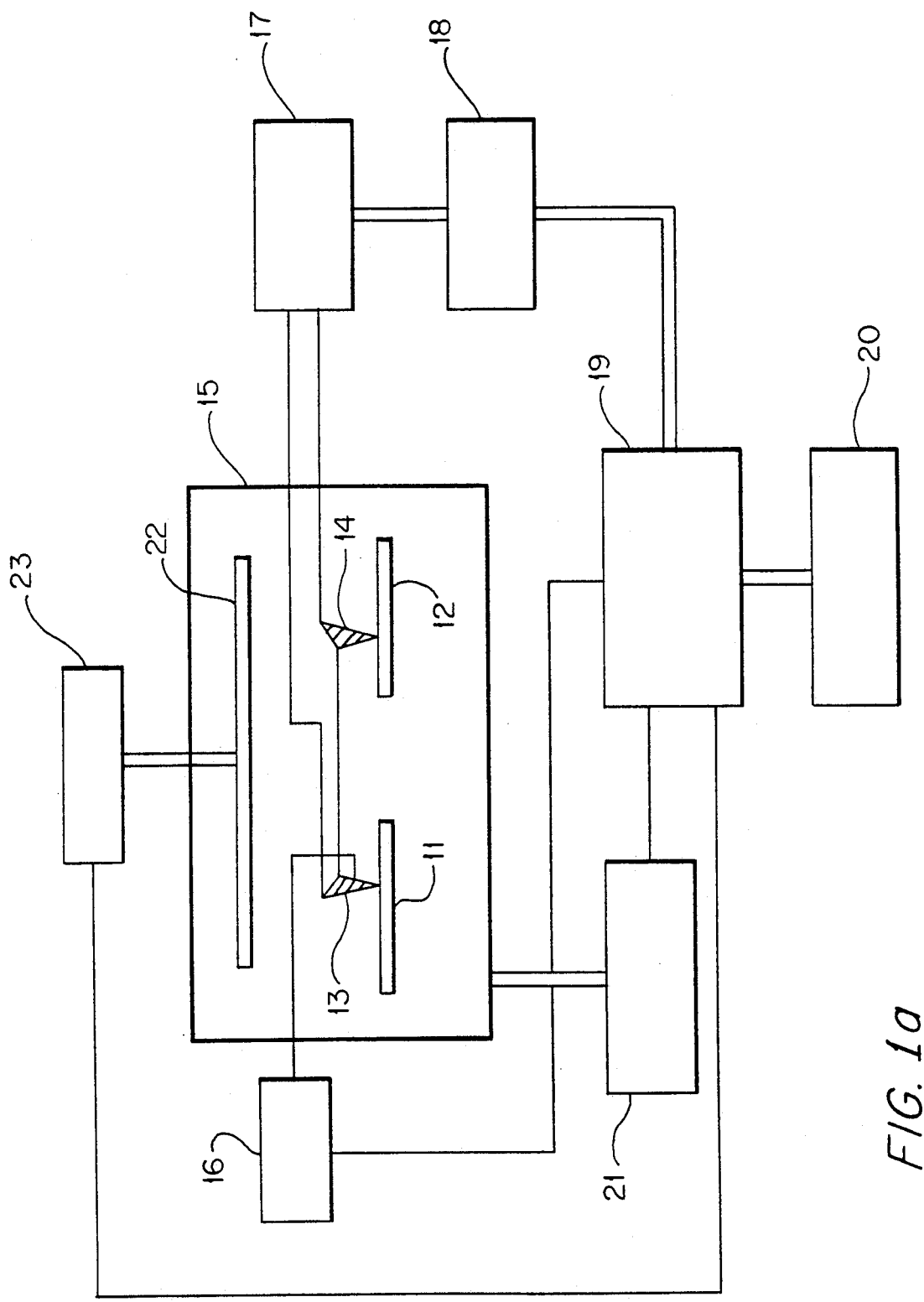
FIG. 1a is a schematic diagram of a spatialy resolved modulated differential analysis apparatus using a furnace.

The present invention is shown schematically in FIG. 1a. FIG. 1a shows a sample 11 and a reference 12, with a thermocouple probe 13 and a reference thermocouple 14 in a furnace 15. The position of the thermocouple probe 13 on sample 11 is controlled by positioning means 16. Positioning means 16 may be partially outside the furnace, as shown in FIG. 1a, or it may be wholly within the furnace. The data from thermocouple probe 13 and reference thermocouple 14 is recorded by recording means 17, and stored in storing means 18. Storing means 18 could comprise a semiconductor memory, and/or magnetic data storage means such as a floppy disk, a hard drive, or magnetic tape. The data could flow from recording means 17 directly to storing means 18, or it could first flow to computer 19, and then to storing means 18. For example, storing means 18 could be the hard disk of computer 19. Computer 19 is used to enter instructions for temperature controller 21 and positioning means 16. Computer 19 is also used to deconvolute and analyze the data. Display means 20, e.g., a CRT, a printer or an x-y plotter, is used to display the results of the analysis. The temperature of both sample 11 and reference 12 is modulated at a modulation frequency $f_m$ by temperature controller 21. The differential temperature measured by thermocouple probe 13 and reference thermocouple 14 is a measure of the difference in the heat flow in the sample to the point below the thermocouple probe, and the heat flow in the reference to the point below the reference thermocouple. Thermocouple probe 13 is scanned over the surface of sample 11 by scanning means 16 to provide a spatially-resolved characterized image of the sample.

Figure 1B:
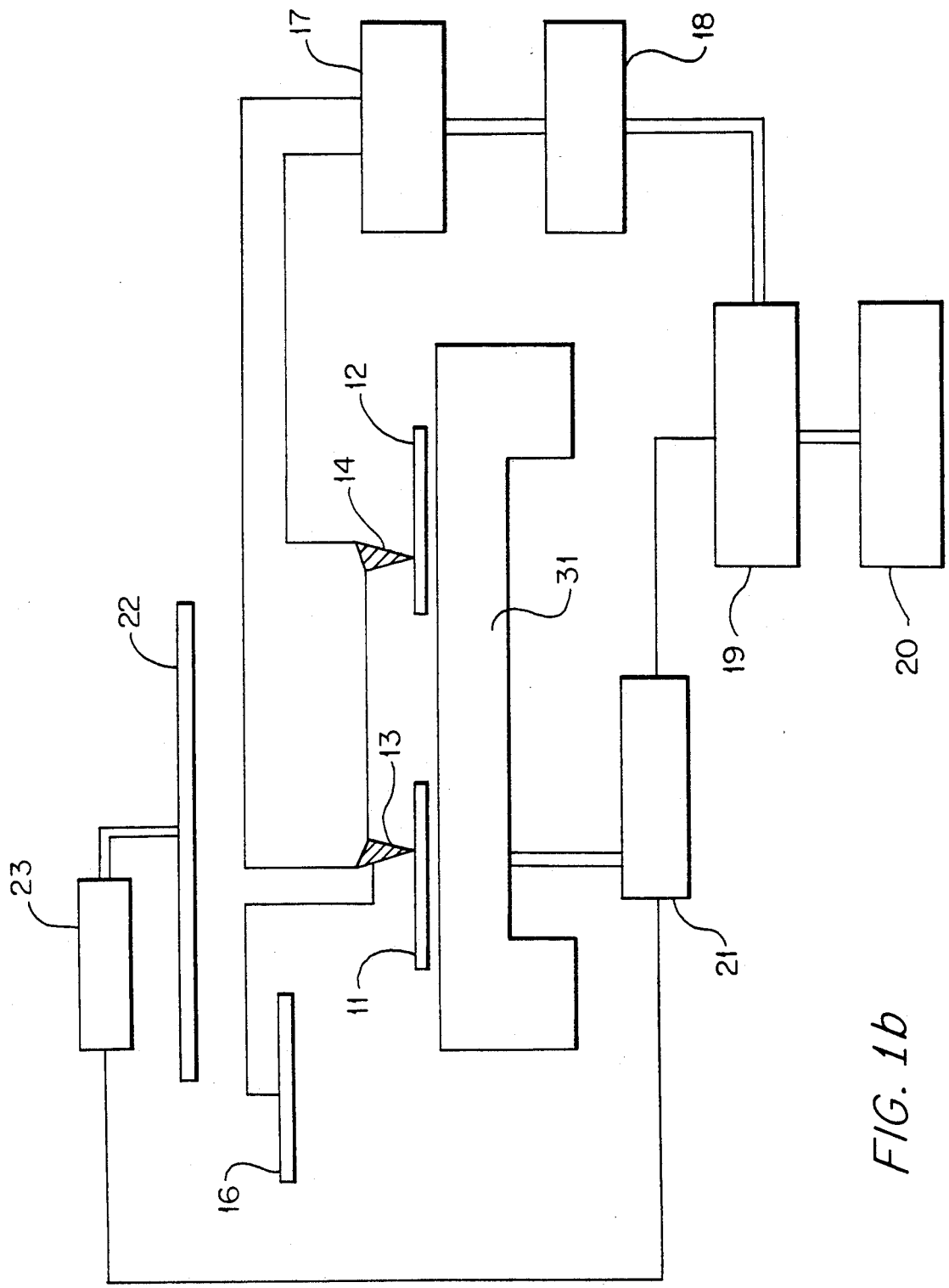
FIG. 1b is a schematic diagram of a spatially resolved differential analysis apparatus using a hot stage.

FIG. 1b shows the present invention implemented using a hot stage 31 instead of a furnace. A hot stage is the preferred apparatus for controlling the temperature of the sample and reference. The temperature of the hot stage is controlled by temperature controller 21, which is in communication with computer 19.

Sample 11 and reference 12 could be placed adjacent to each other in a controlled thermal environment, such as in a furnace or on a hot stage. The temperature of the sample and reference could be modulated by modulating the temperature of the furnace or oven, or by modulating the flow or the temperature of a fluid passing over the sample and the reference. Any periodic modulation waveform could be used, including sinusoidal, square, triangular or sawtooth waveforms.

Figure 2A:
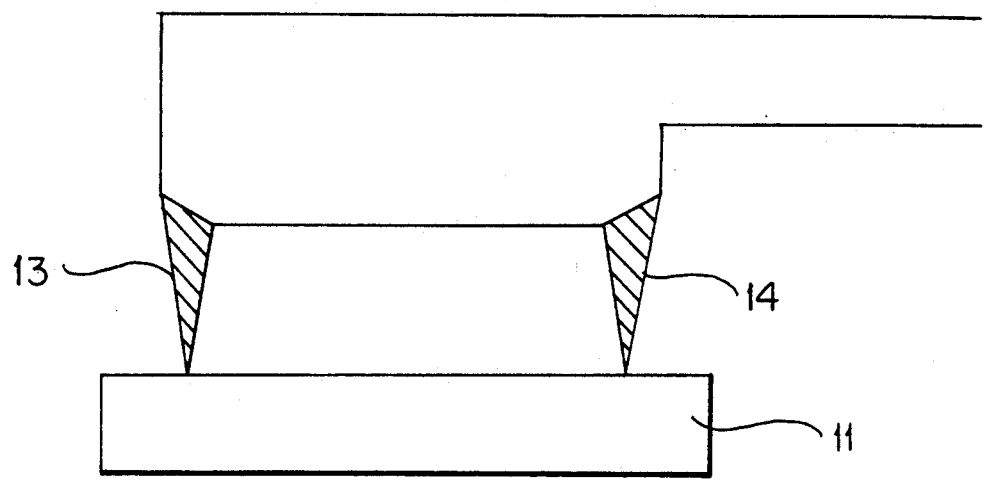
FIGS. 2a and 2b are schematic representations showing how the reference thermocouple can be placed on the sample.
Figure 2B:
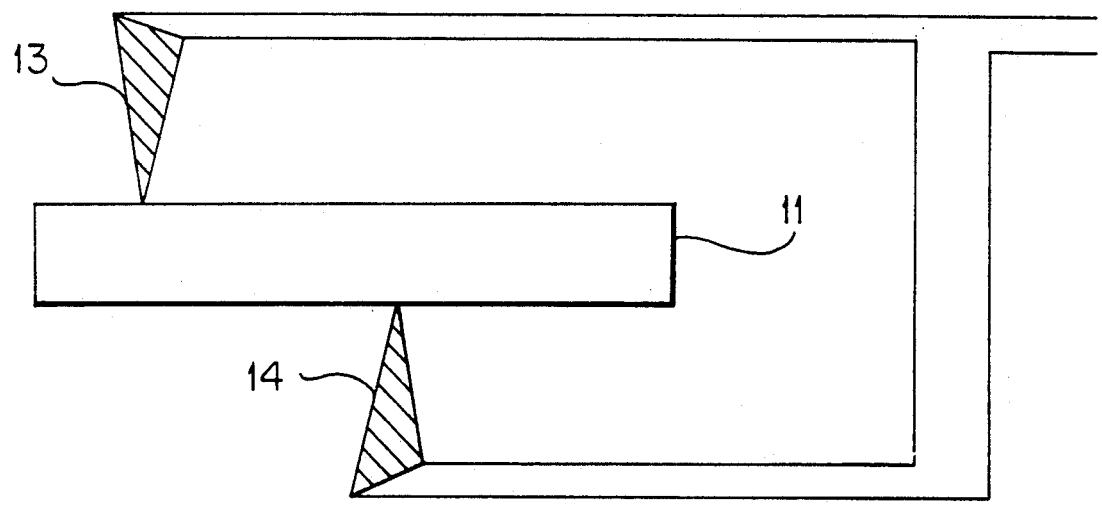

Alternatively, the reference thermocouple may be placed on the sample itself, i.e., one position on the sample could be used as the reference for the other positions on the sample, as shown in FIG. 2a. The reference thermocouple could also be placed in contact with the sample on the opposite side of the probe thermocouple, as shown in FIG. 2b.

Radiant heating means for implementing the second embodiment of the present invention are shown in FIG. 1a and FIG. 1b. The second embodiment comprises two means for periodically varying the temperature of the sample and the reference: furnace 15 or hot stage 31, and radiant heating source 22. The temperature of the furnace or hot stage would be controlled by temperature controller 21. The radiant heating source would be controlled by radiant source controller 23. For example, source controller 23 could impose a sinusoidal modulation onto the power to radiant heating source 22. Computer 19 supplies the appropriate input for furnace controller 21 and radiant source controller 23. In a typical application, the temperature of the sample would be modulated at, e.g., ±1°, 2° or 3° C. at a relatively high modulation rate, e.g., 1–100 Hz by the radiant heating source. The sample would also be subjected to a temperature oscillation of, e.g., ±5°, 10° or 20° C. at a much slower rate, e.g., at 0.01–1 Hz, by varying the temperature of furnace 15 or hot stage 31.

A preferred method for implementing the present invention comprises the following steps:

STEP 1. Selecting a modulation temperature.

STEP 2. Selecting a modulation frequency.

STEP 3. Selecting a modulation amplitude.

STEP 4. Selecting a pattern of predetermined positions over the sample.

STEP 5. Positioning a thermocouple probe over the sample at an initial predetermined position.

STEP 6. Applying a sinusoidal modulation to the temperature selected in step 1, at the frequency selected in step 2 and at the amplitude selected in Step 3.

STEP 7. Monitoring the signal of the thermocouple probe.

STEP 8. Monitoring the differential heat flow.

STEP 9. Deconvoluting the sample temperature and differential heat flow into rapidly reversible and non-rapidly reversible components of heat flow.

STEP 10. Combining the rapidly reversible and non-rapidly reversible components of heat flow to construct the total heat flow at the underlying heating rate. However, this step is not required for all applications.

STEP 11. Repeating STEPS 6–10 at each of the predetermined positions over the sample.

STEP 12. Calculating one or more two-dimensional images based upon one or more of the heat flows obtained in STEPS 9 and 10. The images may be based upon the rapidly reversible or the non-rapidly reversible components of the heat flow, or upon the total heat flow.

STEP 13. Selecting a new temperature and repeating steps 2–12.

STEP 13 may be repeated for each transition temperature, such as at the glass transition for polymer phases, and at the melting point for crystalline phases. The transition temperatures may be determined in a preliminary step, in which the characteristics of the entire sample are obtained according to the modulated differential scanning calorimetry technique described in the parent application.

For example, the sample could be a composite X-Y, consisting of a heterogeneous mixture of a crystalline domain X and an amorphous domain Y. If crystalline domain X had a melting temperature $T_m$ at 500° C., then the modulation temperature could be set to 500° C., with a sinusoidal modulation having a modulation amplitude ±2° C., and a modulation frequency of 0.05 Hz. The thermocouple probe could be moved over a rectangular grid in increments of 200-500 nm. Because the signal from crystalline phase X would be very different from the signal from amorphous phase Y, contrast between the X and Y phases could easily be achieved.

The procedure of STEPS 1-13 may be modified in several ways. For example, the thermocouple probe may be scanned continuously over the sample in a predetermined pattern, instead of being positioned over predetermined positions as in STEP 5. In that case, the scanning rate must be selected such that STEPS 1-13 can be performed within a time interval determined by the required spatial resolution.

In the first embodiment of the present invention, the modulation of the sample and reference temperature achieves two goals in a single step: increasing the signal-to-noise ratio of the differential thermal technique, as described in the parent application, and delineating the different regions of the sample by modulating the temperature of the sample and reference above and below a transition temperature for one phase of the sample material. In the second embodiment of the present invention, these two goals are achieved using two separate steps at two separate frequencies.

The two frequencies are designated as the modulation frequency $f_m$ and an oscillation frequency $f_o$. As an example, the temperature of the sample could be modulated at a frequency ranging from 1 to 100 Hz, at an amplitude of ±1°-3° C., using radiant heating source 22, by controlling the power input to radiant heating source 22 with controller 23. The temperature oscillations could be produced by controlling the temperature of hot stage 31, using a sinusoidal waveform with an amplitude of ±5°-10° C., at a frequency ranging from 0.01 to 0.1 Hz.

For example, a sample of butadiene rubber in a cross-linked expoxy resin could have a transition temperature $T_{g\text{-}rubber} = -50°$ C. for the rubber phase, and a transition temperature $T_{g\text{-}epoxy} = +100°$ C. The rubber phase regions could be identified by, for example, selecting the modulation temperature at −50° C., the modulation frequency at 2 Hz, and the modulation amplitude at ±1° C. The oscillation amplitude could be selected at ±5° C. at a frequency of 0.1 Hz. These temperature variations could be achieved by using (1) a cryogenic source such as liquid nitrogen to cool the apparatus down to, e.g., 78° K.; (2) a hot stage to control the temperature of the sample and reference at temperatures above 78° K. and to provide the temperature oscillation; and (3) a radiation source to provide temperature modulations. The rubber phase will be identifiable because its thermal properties will be changing in phase with the temperature oscillations, whereas the epoxy phase will be comparatively unaffected by the temperature oscillations.

The epoxy phase could be identified by choosing, for example, a sinusoidal waveform, a modulation temperature of 100° C., a modulation amplitude of ±1° C., a modulation frequency of 5 Hz, an oscillation amplitude of ±10° C. and an oscillation frequency of 0.2 Hz.

In an alternative method for applying the second embodiment, the DSC spectrum of the entire sample is obtained using modulated differential scanning calorimetry, as described in the parent invention. The oscillating modulated DSC technique described as the second preferred embodiment of the present invention is then scanned over the sample successively at each of the transition temperatures identified in the modulated DSC measurement. The oscillation amplitude is chosen to cross over one of the transition temperatures in each of the successive scans over the sample.

In the third preferred embodiment of the present invention, a probe is positioned over a region of one phase of the material, as the modulated differential scanning calorimetric technique described in the parent application is applied to obtain a modulated DSC spectrum of that phase. Alternatively, a plurality of probes could be used, with one probe positioned over one region of each phase in the sample, or possibly over each region.

A fourth embodiment of the present invention comprises using an array of probes to obtain differential analysis data simultaneously at a plurality of positions on the sample. For example, a linear array of N probes spaced 500 nm apart along the x-axis could be stepped in 500 nm steps to M positions along the y-axis to obtain an array of N×M data points. This array would require the use of N data channels. Alternatively, an N×M area array using N×M data channels could be used to obtain all the data simultaneously. In either the linear or area alternatives of the fourth embodiment, the sample temperature could be scanned over a relatively wide range, e.g., from cryogenic temperatures to over 1,000° C. This approach would be most useful when the sample is completely unknown, i.e., the operator does not know before the analysis which temperature range or transition temperatures to use. The fourth embodiment could also be used when the transitions are irreversible.

Higher frequencies allow higher spatial resolution, e.g., resolutions of tens of nanometers. For example, frequencies in the megahertz range can be used to probe only material very near the surface.

The present invention could also be applied using other analytical techniques. For example, the present invention could be applied to measure the dielectric properties of a heterogeneous sample having at least two phases using a capacitance probe. The temperature of the sample could be modulated above and below a transition in the dielectric properties of one phase of the sample as the capacitance probe is scanned over the surface of the sample.

The present invention could also be used with an atomic force probe. An atomic force probe is scanned over the surface of a heterogeneous sample, containing at least two phases, as the temperature of the sample is modulated. If the two phases have different coefficients of thermal expansion, the atomic force probe will delineate the regions of each phase. Similarly, the present invention could be used with a magnetic sensor, by modulating the temperature of the sample above and below, e.g., the Curie temperature of a ferromagnetic phase in the material. Optical properties of a material such as reflectance, transmittance or polarization state (e.g., for liquid crystals), could be monitored with a probe such as a laser beam as the sample temperature is modulated above and below a reversible transition in the material.

The present invention could also be implemented using thermoacoustic characterization techniques. The article "Photoacoustic Microscopy," by A. Rosencwaig, published in *International Laboratory*, pages 37–43 (September/October 1979), discusses the use of photoacoustic techniques for microscopy. A laser modulated at a high frequency, e.g., at 20 MHz, modulates the temperature of a sample locally ±1°–3° C. about a transition temperature for one phase of the sample. The laser beam is scanned over the surface of the sample, as a fixed piezoelectric sensor in direct contact with the surface detects acoustic signals. Alternatively, an acoustic microphone may be used to detect the signals.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A spatially-resolved modulated differential analysis apparatus comprising:
   (a) means for controlling the driving variable of a sample material;
   (b) means for selecting a modulation function, a modulation frequency, a modulation amplitude and a modulation value for the driving variable;
   (c) means for modulating the driving variable according to the selected modulation function, modulation frequency and modulation amplitude at the modulation value of the driving variable;
   (d) probe means for detecting spatially-resolved differential changes in a characterizing physical parameter in a localized area of the sample material with respect to a reference;
   (e) means for scanning the probe means across the sample;
   (f) means for recording a signal representative of differential changes in the characterizing physical parameter as a function of the position of the probe on the sample;
   (g) means for storing the signal as data; and
   (h) means for deconvoluting the data to obtain a characterized image of the sample.

2. The apparatus of claim 1, wherein the driving variable is temperature.

3. The apparatus of claim 2, wherein the means for modulating the temperature comprises an electric heater element.

4. The apparatus of claim 2, further comprising means for selecting an oscillation frequency and an oscillation amplitude, and means for varying the temperature of the sample according to the selected oscillation frequency and amplitude.

5. The apparatus of claim 4, wherein the reference is a fixed thermal sensor in thermal contact with the sample.

6. The apparatus of claim 5, wherein the sample has a front surface and a back surface, and the probe means is scanned across the front surface of the sample and the reference is in thermal contact with the back surface of the sample.

7. The apparatus of claim 1, further comprising means for selecting a pattern of sequential positions on the sample for recording data, wherein the probe means is scanned in steps from one position to the next position, and the signal representing the characterizing physical parameter is recorded at each position.

8. The apparatus of claim 7, further comprising means for selecting an oscillation frequency and an oscillation amplitude, and means for varying the driving variable according to the selected oscillation frequency and amplitude.

9. The apparatus of claim 1, wherein the probe means is scanned continuously across the sample, and the signal representing the characterizing physical parameter is recorded continuously.

10. The apparatus of claim 1, further comprising means for selecting an oscillation frequency and an oscillation amplitude, and means for varying the driving variable according to the selected oscillation frequency and amplitude.

11. The spatially-resolved modulated differential analysis apparatus of claim 1, wherein the modulated differential analysis apparatus is a differential scanning calorimeter, the driving variable is temperature, and the characterizing physical parameter is the heat flow to and from the sample.

12. The apparatus of claim 11, further comprising means for selecting an oscillation frequency and an oscillation amplitude, and means for varying the temperature of the sample according to the selected oscillation frequency and amplitude.

13. The apparatus of claim 11, wherein the sample has a front surface and a back surface, and the probe means is scanned across the front surface of the sample and the reference is in thermal contact with the back surface of the sample.

14. The apparatus of claim 11, further comprising means for selecting a pattern of sequential positions on the sample for recording data, wherein the probe means is scanned in steps from one position to the next position, and the signal representing the characterizing physical parameter is recorded at each position.

15. The apparatus of claim 14, further comprising means for selecting an oscillation frequency and an oscillation amplitude, and means for varying the driving variable according to the selected oscillation frequency and amplitude.

16. A spatially-resolved modulated differential calorimeter comprising:
   (a) means for controlling the temperature of a sample material;
   (b) means for selecting a modulation function, a modulation frequency, a modulation amplitude and a modulation temperature;
   (c) means for modulating the temperature according to the selected modulation function, modulation frequency and modulation amplitude at the modulation temperature;
   (d) probe means for detecting spatially-resolved differential changes in the temperature of a localized area of the sample material with respect to a reference;
   (e) means for scanning the probe means across the sample;
   (f) means for recording calorimetric data as a function of position of the probe on the sample;
   (g) means for storing the data; and
   (h) means for deconvoluting the data to obtain a characterized image of the sample.

17. The calorimeter of claim 15, wherein the means for modulating the temperature comprises an electric heater element.

18. The calorimeter of claim 16, further comprising means for selecting an oscillation frequency and an oscillation amplitude, and means for varying the temperature of the sample according to the selected oscillation frequency and amplitude.

19. The calorimeter of claim 18, wherein the reference is a fixed thermal sensor in thermal contact with the sample.

20. The calorimeter of claim 19, wherein the sample has a front surface and a back surface, and the probe means is scanned across the front surface of the sample and the reference is in thermal contact with the back surface of the sample.

21. The calorimeter of claim 16, further comprising means for selecting a pattern of sequential positions on the sample for recording calorimetric data, wherein the probe means is scanned in steps from one position to the next position, and the calorimetric data is recorded at each position.

22. The calorimeter of claim 21, further comprising means for selecting an oscillation frequency and an oscillation amplitude, and means for varying the temperature according to the selected oscillation frequency and amplitude.

23. The calorimeter of claim 22, wherein the means for varying the temperature according to the selected oscillation frequency and amplitude comprises radiant heating means.

24. The calorimeter of claim 16, wherein the probe means is scanned continuously across the sample, and the calorimetric data is recorded continuously.

25. The calorimeter of claim 24, further comprising means for selecting an oscillation frequency and an oscillation amplitude, and means for varying the temperature according to the selected oscillation frequency and amplitude.

26. The spatially-resolved modulated calorimeter of claim 16, wherein the calorimeter is a differential scanning calorimeter.

27. The calorimeter of claim 26, further comprising means for selecting an oscillation frequency and an oscillation amplitude, and means for varying the temperature of the sample according to the selected oscillation frequency and amplitude.

28. The calorimeter of claim 26, further comprising means for selecting a pattern of sequential positions on the sample for recording calorimetric data, wherein the probe means is scanned in steps from one position to the next position, and the calorimetric data is recorded at each position.

29. The calorimeter of claim 28, further comprising means for selecting an oscillation frequency and an oscillation amplitude, and means for varying the temperature according to the selected oscillation frequency and amplitude.

30. A method for obtaining a characterized image of a sample comprising the steps of:
(a) selecting a pattern of positions on a sample;
(b) placing a temperature-sensing probe over a sample at a first position;
(c) obtaining calorimetric data;
(d) storing the calorimetric data;
(e) moving the temperature-sensing probe over the sample to a next position;
(f) repeating steps (b)-(d) at each of the positions in the pattern of positions selected in step (a), and repeating step (e) at each of the positions in the pattern of positions except for the last position in the pattern; and
(g) deconvoluting the calorimetric data to obtain a characterized image of the sample.

31. The method of claim 30, further comprising the steps of:
(h) selecting a modulation cycle characterized by a modulation temperature, a modulation amplitude, and a modulation frequency; and
(i) modulating the sample at the modulation temperature, the modulation frequency, and the modulation amplitude,
wherein step (h) is performed before step (b), and step (i) is performed concurrently with steps (c)-(e).

32. The method of claim 31, further comprising the steps of:
(j) selecting an oscillation cycle characterized by an oscillation amplitude and an oscillation frequency; and
(k) varying the temperature of the sample at the oscillation frequency and the oscillation amplitude,
wherein step (j) is performed before step (b), and step (k) is performed concurrently with steps (c)-(e) and step (h).

33. The method of claim 32, wherein the sample comprises a first material phase and a second material phase, wherein the first material phase is characterized by a transition temperature, and wherein the oscillation amplitude is selected such that the temperature of the sample crosses the transition temperature during the oscillation cycle.

34. The method of claim 33, further comprising the step of identifying regions in the characterized image of the sample that change their appearance in the characterized image at the oscillation frequency, as regions of the first material phase.

35. The method of claim 31, wherein the sample comprises a first material phase and a second material phase, and wherein the first material phase is characterized by a transition temperature, wherein the modulation temperature and modulation amplitude are selected such that the temperature of the sample crosses the transition temperature during the modulation cycle.

36. The method of claim 35, further comprising the step of identifying regions of the sample exhibiting the greatest contrast in the characterized image as being regions of the first phase.

37. The method of claim 34, wherein the calorimetric data is differential scanning calorimetric data.

38. The method of claim 37, further comprising the steps of:
(h) selecting a modulation cycle characterized by a modulation temperature, a modulation amplitude, and a modulation frequency; and
(i) modulating the sample at the modulation temperature, the modulation frequency, and the modulation amplitude,
wherein step (h) is performed before step (b), and step (i) is performed concurrently with steps (c)-(e).

39. The method of claim 38, further comprising the steps of:
(j) selecting an oscillation cycle characterized by an oscillation amplitude and an oscillation frequency; and
(k) varying the temperature of the sample at the oscillation frequency and the oscillation amplitude,
wherein step (j) is performed before step (b), and step (k) is performed concurrently with steps (c)-(e) and step (h).

40. The method of claim 39, wherein the sample comprises a first material phase and a second material phase, wherein the first material phase is characterized by a transition temperature, and wherein the oscillation amplitude is selected such that the temperature of the sample crosses the transition temperature during the oscillation cycle.

41. The method of claim 40, further comprising the step of identifying regions in the characterized image of the sample that change their appearance in the characterized image at the oscillation frequency, as regions of the first material phase.

42. The method of claim 38, wherein the sample comprises a first material phase and a second material phase, and wherein the first material phase is characterized by a transition temperature, wherein the modulation temperature and modulation amplitude are selected such that the temperature of the sample crosses the transition temperature during the modulation cycle.

43. The method of claim 42, further comprising the step of identifying regions of the sample exhibiting the greatest contrast in the characterized image as being regions of the first phase.

44. A method for obtaining a characterized image of a sample comprising the steps of:
(a) selecting a sequence of linear patterns of positions on a sample;
(b) placing a temperature-sensing probe over a sample at each of the positions at the first linear pattern;
(c) obtaining calorimetric data from each of the temperature-sensing probes;
(d) storing the calorimetric data;
(e) moving the temperature-sensing probes over the sample to the next linear pattern of positions on the sample;
(f) repeating steps (b)-(d) at each of the linear patterns of positions selected in step (a), and step (e) at each of the linear pattern of positions except for the last of the linear pattern of positions; and
(g) deconvoluting the calorimetric data to obtain a characterized image of the sample.

45. The method of claim 44, further comprising the steps of:
(h) selecting a modulation cycle characterized by a modulation temperature, a modulation amplitude, and a modulation frequency; and
(i) modulating the sample at the modulation temperature, the modulation frequency, and the modulation amplitude,
wherein step (h) is performed before step (b), and step (i) is performed concurrently with steps (c)-(e).

46. The method of claim 45, further comprising the steps of:
(j) selecting an oscillation cycle characterized by an oscillation amplitude and an oscillation frequency; and
(k) varying the temperature of the sample according to the oscillation cycle at the oscillation frequency and at the oscillation amplitude,
wherein step (j) is performed before step (b), and step (k) is performed concurrently with steps (c)-(e) and step (h).

47. A spatially-resolved modulated differential calorimeter comprising:
(a) means for controlling the temperature of a sample material;
(b) a plurality of probe means at a plurality of positions for detecting spatially-resolved differential changes in the temperature of the sample material with respect to a reference;
(c) means for recording calorimetric data from each probe means;
(d) means for storing the data; and
(e) means for deconvoluting the data to obtain a characterized image of the sample.

48. The apparatus of claim 47, further comprising:
(f) means for selecting a modulation cycle characterized by a modulation temperature, a modulation amplitude, and a modulation frequency; and
(g) means for modulating the sample at the modulation temperature, the modulation frequency, and the modulation amplitude.

49. The apparatus of claim 48, further comprising:
(h) means for selecting an oscillation cycle characterized by an oscillation amplitude and an oscillation frequency; and
(i) means for varying the temperature of the sample according to the oscillation cycle, at the oscillation frequency and at the oscillation amplitude.

50. The calorimeter of claim 47, wherein the plurality of probe means forms a linear array of probe means, further comprising means for scanning the linear array along the sample to a plurality of positions.

51. The apparatus of claim 30, further comprising:
means for selecting a modulation cycle characterized by a modulation temperature, a modulation amplitude, and a modulation frequency; and
means for modulating the sample at the modulation temperature, the modulation frequency, and the modulation amplitude.

52. The apparatus of claim 31, further comprising:
means for selecting oscillation cycle characterized by an oscillation amplitude and an oscillation frequency; and
means for varying the temperature of the sample according to the oscillation cycle at the oscillation frequency and at the oscillation amplitude.

53. The spatially-resolved modulated differential calorimeter of claim 47, wherein the differential calorimeter is a differential scanning calorimeter, and the calorimetric data is differential scanning calorimetric data.

54. The spatially-resolved modulated differential calorimeter of claim 53, further comprising:
(f) means for selecting a modulation cycle characterized by a modulation temperature, a modulation amplitude, and a modulation frequency; and
(g) means for modulating the sample at the modulation temperature, the modulation frequency, and the modulation amplitude.

55. The apparatus of claim 54, further comprising:
(h) means for selecting an oscillation cycle characterized by an oscillation amplitude and an oscillation frequency; and
(i) means for varying the temperature of the sample according to the oscillation cycle, at the oscillation frequency and at the oscillation amplitude.

56. A method for obtaining a characterized image of a sample comprising the steps of:
(a) selecting a pattern of positions on a sample;
(b) placing a temperature-sensing probe over a sample at each of the positions in the pattern of positions;
(c) obtaining calorimetric data from each of the temperature-sensing probes;
(d) storing the calorimetric data; and
(e) deconvoluting the calorimetric data to obtain a characterized image of the sample.

57. The method of claim 56, further comprising the steps of:
(f) selecting a modulation cycle characterized by a modulation temperature, a modulation amplitude, and a modulation frequency; and
(g) modulating the sample at the modulation temperature, the modulation frequency, and the modulation amplitude,
wherein step (f) is performed before step (b), and step (g) is performed concurrently with steps (b)–(d).

58. The method of claim 57, further comprising the steps of:
(h) selecting an oscillation cycle characterized by an oscillation amplitude and an oscillation frequency; and
(i) varying the temperature of the sample according to the oscillation cycle at the oscillation frequency and at the oscillation amplitude,
wherein step (h) is performed before step (b), and step (i) is performed concurrently with steps (b)–(d) and step (g).

59. The method of claim 58, wherein the sample comprises regions of a first phase and regions of a second phase, the first phase having a transition temperature, wherein the oscillation amplitude is selected to cross the transition temperature, further comprising the step of identifying the regions in the image of the sample changing their contrast in phase with the temperature oscillations as regions of the first phase.

60. The method of claim 56, wherein the calorimetric data is differential scanning calorimetric data.

61. The method of claim 60, further comprising the steps of:
(f) selecting a modulation cycle characterized by a modulation temperature, a modulation amplitude, and a modulation frequency; and
(g) modulating the sample at the modulation temperature, the modulation frequency, and the modulation amplitude,
wherein step (f) is performed before step (b), and step (g) is performed concurrently with steps (b)–(d).

62. The method of claim 61, further comprising the steps of:
(h) selecting an oscillation cycle characterized by an oscillation amplitude and an oscillation frequency; and
(i) varying the temperature of the sample according to the oscillation cycle at the oscillation frequency and at the oscillation amplitude,
wherein step (h) is performed before step (b), and step (i) is performed concurrently with steps (b)–(d) and step (g).

63. A method for obtaining a characterized image of a sample comprising:
(a) placing a sample in an apparatus comprising means for controlling the driving variable of the sample, a differential probe means, and means for scanning the differential probe means over a sample;
(b) selecting a modulation function, a modulation frequency, a modulation amplitude and a modulation value for the driving variable;
(c) modulating the driving variable according to the selected modulation function, modulation frequency and modulation amplitude at the modulation value of the driving variable;
(d) detecting differential changes in a characterizing physical parameter in a localized area of the sample material with respect to a reference;
(e) scanning the probe means across the sample;
(f) recording a signal representative of differential changes in the characterizing physical parameter as a function of the position of the probe on the sample;
(g) storing the signal as data; and
(h) deconvoluting the data to obtain a characterized image of the sample.

64. The method of claim 63, further comprising the steps of selecting an oscillation frequency and an oscillation amplitude, and varying the driving variable of the sample according to the selected oscillation frequency and amplitude.

65. The method of claim 63, further comprising the steps of selecting a pattern of sequential positions on the sample for recording data, scanning the probe means in steps from one position to the next position, and recording the signal representing the characterizing physical parameter at each position.

66. The method of claim 65, further comprising selecting an oscillation frequency and an oscillation amplitude, and varying the driving variable according to the selected oscillation frequency and amplitude.

67. The method of claim 63, further comprising the steps of scanning the probe means continuously across the sample, and continuously recording the signal representing the characterizing physical parameter.

68. The method of claim 63, wherein the driving variable is temperature.

69. The method of claim 68, wherein the probe means is a magnetic sensor.

70. The method of claim 68, wherein the probe means is a capacitance probe.

71. The method of claim 68, wherein the probe means is an atomic force probe.

72. The method of claim 68, wherein the probe means is selected from the group consisting of a piezoelectric sensor and an acoustic microphone.

* * * * *